United States Patent
Vogtmeier et al.

(10) Patent No.: US 11,058,377 B2
(45) Date of Patent: Jul. 13, 2021

(54) DEVICE AND METHOD FOR DETERMINING POSITIONING DATA FOR AN X-RAY IMAGE ACQUISITION DEVICE ON A MOBILE PATIENT SUPPORT UNIT

(71) Applicant: KONINKLIJKE PHILIPS N.V., Eindhoven (NL)

(72) Inventors: Gereon Vogtmeier, Aachen (DE); Jens Von Berg, Hamburg (DE); Ravindra Bhat, Eindhoven (NL); Roger Steadman Booker, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 59 days.

(21) Appl. No.: 16/614,114

(22) PCT Filed: May 18, 2018

(86) PCT No.: PCT/EP2018/063225
§ 371 (c)(1),
(2) Date: Nov. 15, 2019

(87) PCT Pub. No.: WO2018/211124
PCT Pub. Date: Nov. 22, 2018

(65) Prior Publication Data
US 2020/0113532 A1    Apr. 16, 2020

(30) Foreign Application Priority Data
May 18, 2017   (EP) ..................................... 17171633

(51) Int. Cl.
*H05G 1/02*    (2006.01)
*A61B 6/00*    (2006.01)

(52) U.S. Cl.
CPC .......... *A61B 6/4405* (2013.01); *A61B 6/4441* (2013.01); *A61B 6/469* (2013.01); *A61B 6/587* (2013.01)

(58) Field of Classification Search
CPC ....... A61B 6/04; A61B 6/0478; A61B 6/0487; A61B 6/08; A61B 6/4405; A61B 6/4441;
(Continued)

(56) References Cited

U.S. PATENT DOCUMENTS 6,608,884 B1   8/2003  Mazess
7,401,977 B2   7/2008  Graumann
(Continued)

FOREIGN PATENT DOCUMENTS

DE     102006059500 A1    7/2008
EP        2380496 A1     10/2011
(Continued)

OTHER PUBLICATIONS

PCT International Search Report, International application No. PCT/EP2018/063225, dated Aug. 16, 2018.

*Primary Examiner* — Irakli Kiknadze
(74) *Attorney, Agent, or Firm* — Larry Liberchuk (57) ABSTRACT

The present invention relates to a device (1) for determining positioning data for an X-ray image acquisition device (2) on a mobile patient support unit (3), the device comprising: a processing unit (10); and a status detector (11); wherein the status detector (11) is configured to acquire geometry data and type data of a mobile patient support unit (3) and of an X-ray image acquisition device (2) on the mobile patient support unit (3), and to transmit a status signal comprising the geometry data and the type data; wherein the processing unit (10) is configured to receive the status signal and data about region of interest position on the patient; and wherein, based on the status signal and the region of interest position, (Continued)

the processing unit (10) is configured to determine positioning and alignment data for an X-ray image acquisition device (2) on the mobile patient support unit (3), and to provide an image acquisition protocol for the X-ray image acquisition device (2). The device (1) may provide an X-ray image acquisition system having a simple and easy to operate construction.

13 Claims, 6 Drawing Sheets

(58) Field of Classification Search
CPC ....... A61B 6/4494; A61B 6/461; A61B 6/469; A61B 6/505; A61B 6/547; A61B 6/548; A61B 6/587; A61B 6/032; A61B 2034/105; A61B 34/10; A61B 6/5205; A61B 2034/107; A61B 2034/2046; A61B 2090/3966; A61B 6/4452; A61B 6/502; A61B 6/105; A61B 6/14; A61B 6/4208; A61B 6/4233; A61B 6/4458; A61B 6/4476; A61B 6/02; A61B 6/025; A61B 6/0414; A61B 34/20; A61B 5/06; A61B 5/107; A61B 5/1071; A61B 5/1075; A61B 5/1079; A61B 5/1121; A61B 5/1128; A61B 5/4528; A61B 5/4566; A61B 5/7275; A61B 5/7278; G06T 11/006; G06T 2211/424; G06T 2207/10004; G06T 2207/10116; G06T 2207/20048; G06T 2207/30012; G06T 7/0012; G06T 7/0014; G06T 7/11; G06T 11/008; G06T 19/00; G06T 2219/008; G06T 2219/012; G16H 30/20; G16H 30/40; H04N 7/18; H04N 7/183
See application file for complete search history.

(56) References Cited

U.S. PATENT DOCUMENTS

| | | | |
|---|---|---|---|
| 10,001,495 B2 | 6/2018 | Sommer | |
| 10,653,385 B2 | 5/2020 | Mehendale | |
| 2001/0036246 A1 | 11/2001 | Graumann | |
| 2003/0004438 A1* | 1/2003 | Berthonnaud | ....... A61B 5/4023 600/595 |
| 2008/0258929 A1 | 10/2008 | Maschke | |
| 2009/0257564 A1 | 10/2009 | Kito | |
| 2011/0135053 A1* | 6/2011 | Noordhoek | ............ A61B 6/583 378/11 |
| 2011/0178384 A1 | 7/2011 | Kuth | |
| 2013/0064344 A1 | 3/2013 | Carol | |
| 2014/0018672 A1 | 1/2014 | Klahr | |
| 2015/0124940 A1 | 5/2015 | Kim | |
| 2015/0228071 A1 | 8/2015 | Jockel | |
| 2015/0302556 A1* | 10/2015 | Birkenbach | ............... G06T 7/33 382/131 |
| 2016/0074000 A1 | 3/2016 | Uehara | |
| 2016/0074003 A1 | 3/2016 | Manke | |

FOREIGN PATENT DOCUMENTS

| | | |
|---|---|---|
| JP | H01123312 U | 8/1989 |
| JP | 2020119485 A | 6/2010 |
| JP | 2011004869 A | 1/2011 |
| WO | WO8503633 A1 | 8/1985 |

* cited by examiner

DEVICE AND METHOD FOR DETERMINING POSITIONING DATA FOR AN X-RAY IMAGE ACQUISITION DEVICE ON A MOBILE PATIENT SUPPORT UNIT

FIELD OF THE INVENTION

The present invention relates to a device for determining positioning data for an X-ray image acquisition device on a mobile patient support unit and a method for determining positioning data for an X-ray image acquisition device on a mobile patient support unit.

BACKGROUND OF THE INVENTION

X-ray imaging may be used to image the skeletal structure of a patient. Common X-ray imaging devices are large C-arm systems and require a complex infrastructure for electricity, image acquisition units, space etc. The infrastructure further provides a constant distance between an X-ray tube and an X-ray detector of the X-ray imaging device. This distance is necessary for focusing the X-ray radiation being emitted from the X-ray tube onto the X-ray detector. Due to the restrictions resulting from the complex infrastructure, there is only a limited number of stationary X-ray imaging devices in hospitals as well as in rural areas.

US2015/0124940A1 describes that an X-ray imaging apparatus may include at least one X-ray detector including a storage unit configured to store ID information and a mounting position detecting unit; at least one mounting unit in which the X-ray detector is mounted; and a control unit configured to determine which X-ray detector among the at least one X-ray detector is mounted in which mounting unit among the at least one mounting unit based on the ID information and an output value of the mounting position detecting unit.

In a rural setting, in an environment at the patient's home or in a nursing home a large C-arm system cannot be provided. However, mobile systems may be used comprising a special mobile chair for holding the region of interest of patient in position and a mobile X-ray imaging system. The complete system geometry is flexible. An operator, usually a nurse, may adjust the mobile components to the patient and the environment.

However, the adjustment of the mobile components is difficult and time consuming since for acquiring useful images of the region of interest in the required magnification, the operator must arrange the correct distances between the X-ray tube and the X-ray detector as well as to the region of interest on the patient.

SUMMARY OF THE INVENTION

There may thus be a need to provide an X-ray imaging system having a simple and easy to operate construction.

The object of the present invention is solved by the subject-matter of the independent claims; further embodiments are incorporated in the dependent claims. It should be noted that the following described aspects of the invention apply also for the system and the method.

In an aspect, there is provided a device for determining positioning data for an X-ray image acquisition device on a mobile patient support unit as defined in appended claim 1.

In another aspect, there is provided a system for determining positioning data for an X-ray image acquisition device on a mobile patient support unit.

In another aspect, there is provided a method for determining positioning data for an X-ray image acquisition device on a mobile patient support unit.

In another aspect, there is provided a computer program element and a computer readable medium.

According to the present invention, a device for determining positioning data for an X-ray image acquisition device on a mobile patient support unit comprises: a processing unit; and a status detector; wherein the status detector is configured to acquire geometry data and type data of a mobile patient support unit and of an X-ray image acquisition device on the mobile patient support unit, and to transmit a status signal comprising the geometry data and the type data; wherein the processing unit is configured to receive the status signal and data about region of interest position on the patient; and wherein, based on the status signal and the region of interest position, the processing unit is configured to determine positioning and alignment data for an X-ray image acquisition device on the mobile patient support unit, and to provide an image acquisition protocol for the X-ray image acquisition device.

The device may automatically determine positioning data for the components of the X-ray image acquisition device and/or for components of the mobile support unit. This means that the device acquires the information about the spatial position as well as the angular orientation of those components. That information may be acquired by the status detector of the device.

The status detector may acquire the type of each component which provides the information about the geometric dimensions as well as an adjustability of the component. For example, if a certain type of a component of the mobile patient support unit may be varied in length, the extension of that variability may be provided by the type information.

The acquired data about geometry and type is used by the device to determine the correct distances and the correct angles of the components. Furthermore, the device provides an image acquisition protocol for the X-ray image acquisition device based on the acquired geometry data and based on the acquired type data. The image acquisition protocol may provide a value for the intensity of the X-ray radiation being emitted by the X-ray tube. The device may amend one or more parameter settings of an image acquisition protocol for adjusting the image acquisition protocol to the acquired geometry and type data. In addition or alternatively, the device may choose an image acquisition protocol from at least two image acquisition protocols which differ in the main protocol properties. Those at least two image acquisition protocols may be stored in a storage unit of the device.

The device therefore provides an easy way to determine the correct distances for the acquisition of X-ray images with a mobile X-ray image acquisition device on a mobile patient support unit. This simplifies the operation of a mobile X-ray image acquisition device on a mobile patient support unit.

Prior to further describing the present invention, a brief description of some terms is provided.

The term type data may be the type of the mobile patient support unit, the type of the components of the mobile patient support unit, the type of the X-ray image acquisition device, and/or the type of the components of the X-ray image acquisition device.

The term geometry data may comprise the position and the alignment data of the components of the mobile patient support unit and/or the components of the X-ray image acquisition device in relation to the mobile support unit.

The term region of interest position may determine the position of the region to be imaged by the X-ray image acquisition device in relation to the mobile patient support unit.

In an example, the status detector may comprise a contact switch, a position detecting element, an RF-ID tag for e.g. identification of different components with different lengths, a sensor for angle detection, a distance controller, an accelerometer, or a gyroscopic sensor e.g. for measuring the inclination angle of a component, etc.

According to an example, the device further comprises: an interface; wherein the interface is configured to provide the positioning and alignment data to an operator and/or receive data about a region of interest position on the patient from the operator.

The interface may provide the information about the positioning and alignment data in visible and/or audible form. Thus, the interface may comprise a monitor and/or boxes. Furthermore, the interface may receive data from the operator in visible, audible and/or gesture form. Thus, the interface increases the simplicity and the handling of the device and the operation of a mobile X-ray image acquisition device on a mobile patient support unit.

According to a further example, the processing unit further comprises: a comparator; wherein the comparator is configured to compare the geometry data to the positioning and alignment data and to provide a result signal comprising the information whether the geometry data matches the positioning and alignment data.

The comparator therefore checks whether the operator has correctly adjusted the components of the X-ray image acquisition device and the mobile patient support unit. If after positioning the components, the geometry data do not match the positioning and alignment data, the comparator may provide a warning signal. The comparator may also provide another signal which indicates that the geometry data matches the positioning and alignment data. This further improves the handling and the simplicity of the device and the alignment of the components of the mobile X-ray image acquisition device and the mobile patient support unit.

In another example, the processing unit comprises: an optimization module; wherein the optimization module is configured to determine an optimized positioning and alignment data and the optimal image acquisition protocol based on the status signal and the region of interest position; and wherein the processing unit is configured to provide an image acquisition protocol based on the optimal image acquisition protocol.

The optimization module optimizes the positioning and alignment data in view of the image quality. This increases the quality of the result of the X-ray acquisition process such that a repetition of the image acquisition process may be avoided.

In an example, the mobile patient support unit comprises connection elements for attaching components of an X-ray image acquisition system to the mobile patient support unit.

According to the present invention, a system for determining positioning data for an X-ray image acquisition device on a mobile patient support unit comprises: a mobile patient support unit; an X-ray image acquisition system; and a device according to the above description; wherein the mobile patient support unit comprises: a support unit; wherein the support unit attaches at least a component of the X-ray image acquisition system to the mobile patient support unit; and wherein the status detector is configured to detect the type and the geometry of the support unit and the mobile patient support unit, wherein the position and the alignment define the geometry data.

The support unit provides a flexible positioning system for the X-ray image acquisition system. The positioning may comprise the distance as well as the angle of the components of the X-ray image acquisition system. Furthermore, the X-ray image acquisition system may be exactly positioned by the support unit.

In an example, a mobile patient support unit may e.g. be a chair, a positioning support, a wheelchair, a special mobile bed, or a table etc. The mobile patient support unit may further comprise fixtures for the patient's body part, e.g. a fixture for a patient's arm.

In an example, the mobile patient support unit comprises: a movement sensor; wherein the movement sensor is adapted to determine a patient's movement on the mobile patient support unit and to provide a movement signal; and wherein the processing unit is adapted to receive the movement signal and further is adapted to determine a point of time for acquiring an X-ray image based on the movement signal.

With the movement sensor, the patient's movement may be monitored and considered in the image acquisition process. Therefore, blurred images are avoided since the image may be acquired when the patient's movements are below a predefined minimum.

In another example, the support unit comprises: at least two support devices; wherein the X-ray image acquisition device comprises: an X-ray tube; and an X-ray detector; wherein at least one of the at least two support devices is attached to the X-ray tube and the at least one of the remaining support devices is attached to the X-ray detector.

In a further example, the at least two support devices comprise a joint connector; and/or a rotational bearing element, wherein the rotational bearing element is connected to the mobile patient support unit, and wherein at least one of the at least two support devices is movably attached to the mobile patient support unit or each support device is configured to provide a fixed mounting for the X-ray tube and the X-ray detector.

In an example the X-ray image acquisition device may comprise an X-ray tube, an X-ray detector, an X-ray generator, an image data acquisition unit and an image data processing unit.

In an example, the mobile patient support unit may comprise fixtures for holding the patient's body parts, e.g. the patient's arm. Further, the mobile patient support unit may comprise a support device, wherein the support device comprises a telescopic element to change the length of the support device.

In an example the joint connector comprises a joint which allows rotational movement around three different rotational axes.

In an example the rotational bearing element may provide a rotational movement of the support device around the mobile patient support unit.

In an example, a further joint connector of a further support device is adapted to connect to a further element of the X-ray image acquisition device.

In an example, the processing unit is further adapted to monitor the position of the components of the mobile patient support unit. Further, the processing unit may provide data for guidance of the operator to let the operator match the proposed positions according to the image acquisition protocols, also based on the data about the components of the support unit. The mobile patient support unit can report whether it was set up well according to a given purpose or what needs to be changed before the acquisition may be done properly.

In an example the imaging position is the optimum imaging position. The imaging position is the position in which the X-ray tube and the X-ray detector are enabled to take an X-ray image from a patient in the mobile patient support unit.

In an example, a focused visible image may be deployed to for finding the correct relative position of the X-ray tube and the X-ray detector depending on the image task. The distance and centre point of the X-ray detector may be found by finding the distance that yields a sharp visible image, i.e. focusing by changing the distance. This further simplifies the operation of the X-ray image acquisition device.

In a further example, the relative position of the X-ray tube and the X-ray detector may be assisted by means of optical guidance. That is, depending on the imaging task, the X-ray tube may project a light guidance, e.g. square grid and frame, which may correspond to the size of the X-ray detector at a given distance. In this way, an operator can locate and fix the X-ray detector when the light grid is fully projected on the X-ray detector. This provides a further simplification of the aligning process of the X-ray image acquisition device.

In an example, the mobile patient support unit comprises positioning elements for the patient's arm, leg, head etc. that is to be imaged.

In an example, a support device may comprise a leg element, wherein the leg element comprises a foot element and a head element, wherein the head element is attached to the joint connector and wherein the foot element is adapted to carry the leg element when the foot element contacts the ground.

In an example, the rotational bearing is attached to the mobile patient support unit; wherein the joint connector is attached to the X-ray tube or the X-ray detector; wherein the processing unit is adapted to receive the position status signal; and wherein the processing unit is adapted to monitor the position status of the joint connector and/or the rotational bearing element in relation to the mobile patient support unit.

Furthermore, according to the present invention, a method for determining positioning data for an X-ray image acquisition device on a mobile patient support unit, the method comprises the following steps: a) acquiring geometry data and type data of a mobile patient support unit and of an X-ray image acquisition device on the mobile patient support unit with a status detector; b) acquiring data about a region of interest position on the patient; c) determining positioning and alignment data for an X-ray image acquisition device on the mobile patient support unit based on the region of interest position data, the geometry data and the type data; and d) providing an image acquisition protocols based on the region of interest position data, the geometry data and the type data; wherein step b) and c) may be performed at the same time or in any order.

In an example, the method further comprises the following step: e) providing the positioning and alignment data to an operator by an interface.

In another example, wherein the method further comprises the following steps: f) comparing the geometry data to the positioning and alignment data with a comparator; and g) providing a result signal comprising the data whether the geometry data matches the positioning and alignment data.

Furthermore, in an example, step c) comprises the substeps: c1) determining the optimized positioning and alignment data and the optimal image acquisition protocol based on the status signal; and c2) determining an image acquisition protocol based on the optimal image acquisition protocol.

In a further example, the method further comprises the following steps: h) determining a patient's movement on a mobile patient support unit; and i) determining a point of time for acquiring an X-ray image of the patient.

In an example, the method is performed automatically.

Further, according to the present invention, a computer program element for controlling an apparatus mentioned above, which, when being executed by a processing unit, is adapted to perform the method steps mentioned above.

Also, according to the present invention, a computer readable medium has stored the program element mentioned above.

These and other aspects of the present invention will become apparent from and be elucidated regarding the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 3:
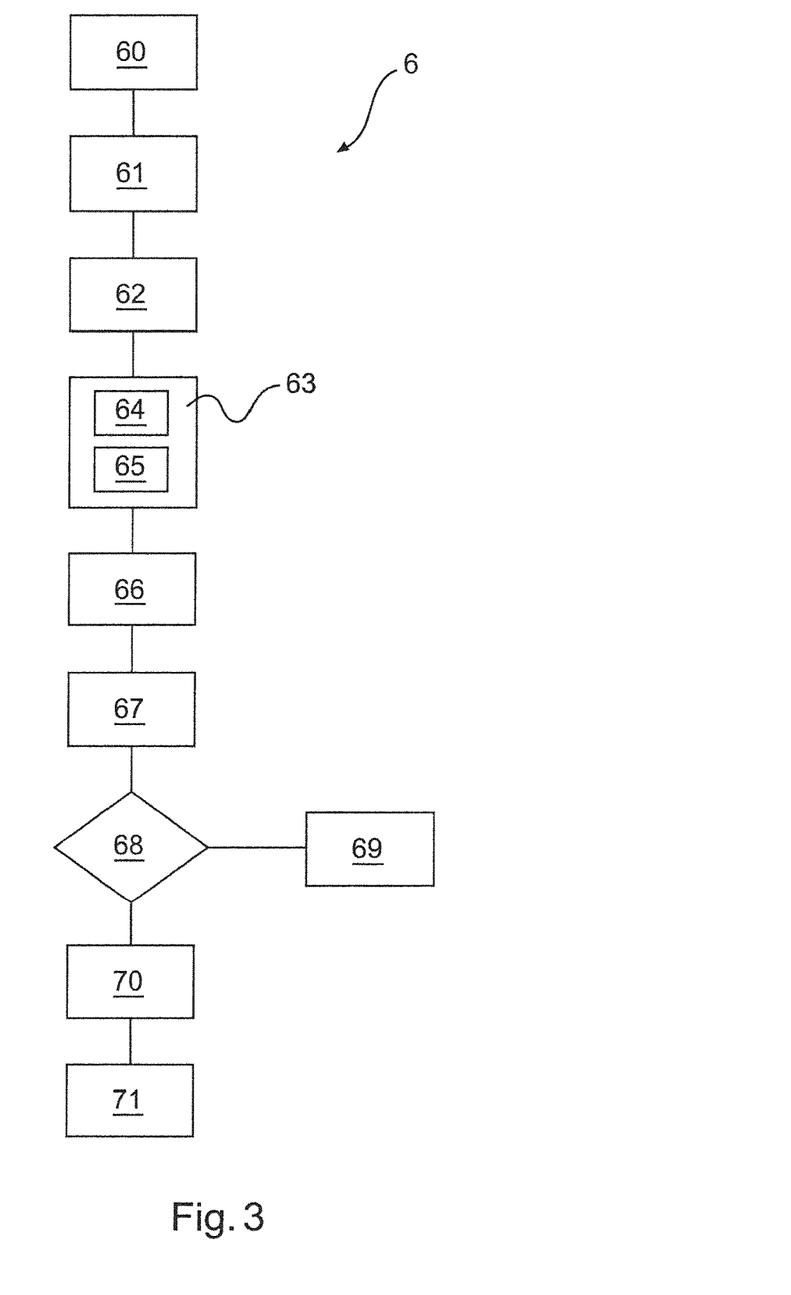
FIG. 3 shows a schematic flow diagram of the method for determining positioning data for an X-ray image acquisition device on a mobile patient support unit.

Before further describing the device and the system, examples of a method are described in further detail referring to FIG. 3.

The method 6 is used for determining positioning data for an X-ray image acquisition device 2 on the mobile patient support unit 3. In a step 60, geometry data and type data of the mobile patient support unit 3 is acquired with a status detector 11. The geometry data comprises the position of the components of the X-ray image acquisition device 2 and the mobile patient support unit 3 in relation to the mobile patient support unit 3. The status detector 11 may collect the geometry data and the type data by questioning geometry sensors 14 and type sensors 16 which are located at the X-ray image acquisition device 2 and the mobile patient support unit 3.

In a further step 61 data about a region of interest position on the patient is acquired. That region of interest may be e.g. a patient's arm, leg or further organ which may be indicated by an operator. The position of that region of interest is then related to the mobile patient support unit 3. With steps 60 and 61 the relevant positions which are needed for the adjustment of the components of the X-ray image acquisition device 2 and the mobile patient support unit 3 may be acquired.

Steps 60 and 61 may be performed at the same time or in any order. It does not matter if the acquisition of the region of interest position data is performed before the acquisition of the geometry data and the type data of the mobile patient support unit 3 and the X-ray image acquisition device 2.

Furthermore, in a further step 62 positioning and alignment data for the X-ray image acquisition device 2 on the mobile patient support unit 3 are determined considering region of interest position data of step 61, the geometry data and the type data being acquired in step 60. Therefore, the method 6 provides the information about the positioning and the alignment for the X-ray image acquisition device components. Using that information, the operator may position and align the X-ray image acquisition device 2 according to the positioning and alignment data to ensure that the acquired image shows the region of interest in the correct magnification and in adequate quality.

In a further step 63 the method provides an image acquisition protocol for the X-ray image acquisition device 2 based on the region of interest position data, the geometry data and the type data. The image acquisition protocol for the X-ray image acquisition device 2 provides the parameters for the image acquisition with the X-ray image acquisition device 2. The image acquisition protocol may for example comprise the values for the voltage and the current for the spectrum and the flux together with the operation time of the X-ray radiation source to determine the X-ray radiation intensity needed for the image acquisition or the time duration for applying the X-ray radiation on the region of interest position.

The provisioning of the image acquisition protocol step 63 may comprise sub-steps. Thereby, in a sub-step 64, an optimized positioning and alignment data and the optimal image acquisition protocol based on the status signal may be determined. This means, that the method performs a check on the image acquisition protocol and the positioning and alignment data. Further, the method may simulate the result of the image acquisition. Based on the simulation the image acquisition protocol and the positioning and alignment data may be altered until the simulation provides the result that an optimized image will be acquired. In a further sub-step 65, the corresponding image acquisition protocol and positioning and alignment data is then determined to be the optimized positioning and alignment data and the optimal image acquisition protocol.

In a further step 66 after step 63, the positioning and alignment data may be provided to an operator by an interface. The operator may then position and align the X-ray image acquisition device 2 based on the position and alignment data which the interface communicates to the operator.

Alternatively, the positioning and alignment data may be used to automatically position and align the components of the X-ray image acquisition device 2. This may further simplify the image acquisition with an X-ray image acquisition device 2.

The method may further comprise the step 67 wherein the geometry data is compared to the positioning and alignment data with a comparator. This comparison may provide any deviations between the positioning and alignment data and the geometry data, wherein the geometry data provides the actual position and alignment of the components of the X-ray image acquisition device 2 and the mobile patient support unit 3. If the deviations are within a threshold interval, the comparison may result that the geometry data match the positioning and alignment data. If not, the comparison would result that the geometry data does not match the positioning and alignment data.

The result may be communicated in a further step 68 in which a result signal comprising the information whether the jump to data matches the positioning and alignment data is provided. If the geometry data does not match the positioning and alignment data, the signal may be an alarm signal which may alarm the operator that the components of the X-ray image acquisition device are not correctly positioned and aligned. Furthermore, the signal according to step 68 may provide a confirmation signal providing the information that the components of the X-ray image acquisition device 2 are correctly aligned and positioned according to the positioning and alignment data.

Furthermore, the method may comprise a step 70 in which a patient's movement on the mobile patient support unit 3 is determined. The determination of the movement of the patient may be performed by a movement sensor 30. The information about the patient's movement may be used in a step 71 in which the point of time for acquiring an X-ray image of the patient is determined. The determination of the point of time for acquiring an X-ray image of the patient may consider how much the patient moves. If the patient moves much then the point of time for acquiring the X-ray image is delayed. The point of time for the acquisition of the X-ray image may be set to the actual point of time, if the patient does not move much. Therefore, that determination of the point of time for the image acquisition may avoid blurring or a reduced image quality due to movements by the patient.

FIG. 1 shows a schematic drawing of a system 7 for determining positioning data for an X-ray image acquisition device 2 on a mobile patient support unit 3. The system 7 comprises a device 1 for determining positioning data for X-ray image acquisition device 2 on a mobile patient support unit 3.

The mobile patient support unit 3 is depicted as a chair in FIGS. 1a to 1d. The mobile patient support unit 3 has a seating platform 31, a back support 32 and arm supports 33. The position of the back support 32 and the arm supports 33 may be altered with respect to the seating platform 31. The position of the back support 32 and the arm supports 33 may be monitored by status sensors 14. The status sensors 14 may provide the position of the back support 32 and the arm supports 33 with respect to the seating platform 31.

Furthermore, the mobile patient support unit 3 comprises a leg 40 which bears the seating platform 31. The leg 40 may be a telescopic element which may have a variable length. Furthermore, the leg 40 may comprise a type sensor 16 which provides the type of the leg 40. The type may e.g. determine how much the leg 40 may be extended.

The leg 40 may comprise rolls 34 to mobilize the mobile patient support unit 3. Further, the leg 40 may comprise stopping elements 35 which immobilize the mobile patient support unit 3 to fix the position of the mobile patient support unit 3.

The mobile patient support unit 3 may further comprise a support unit, having two arms 36 and 41 being connected to the mobile patient support unit 3 by a rotational bearing 38. Due to the rotational bearing 38, the arms 36, 41 may be turned around the mobile patient support unit 3. The arms 36, 41 may comprise joint connectors 39 which allow an angular disposition of at least a portion of the respective arm 36, 41. Furthermore, the arms 36, 41 bear components of the X-ray image acquisition device 2. The rotational bearing 38 may be fixated such that a rotational movement is blocked.

Figure 1A:
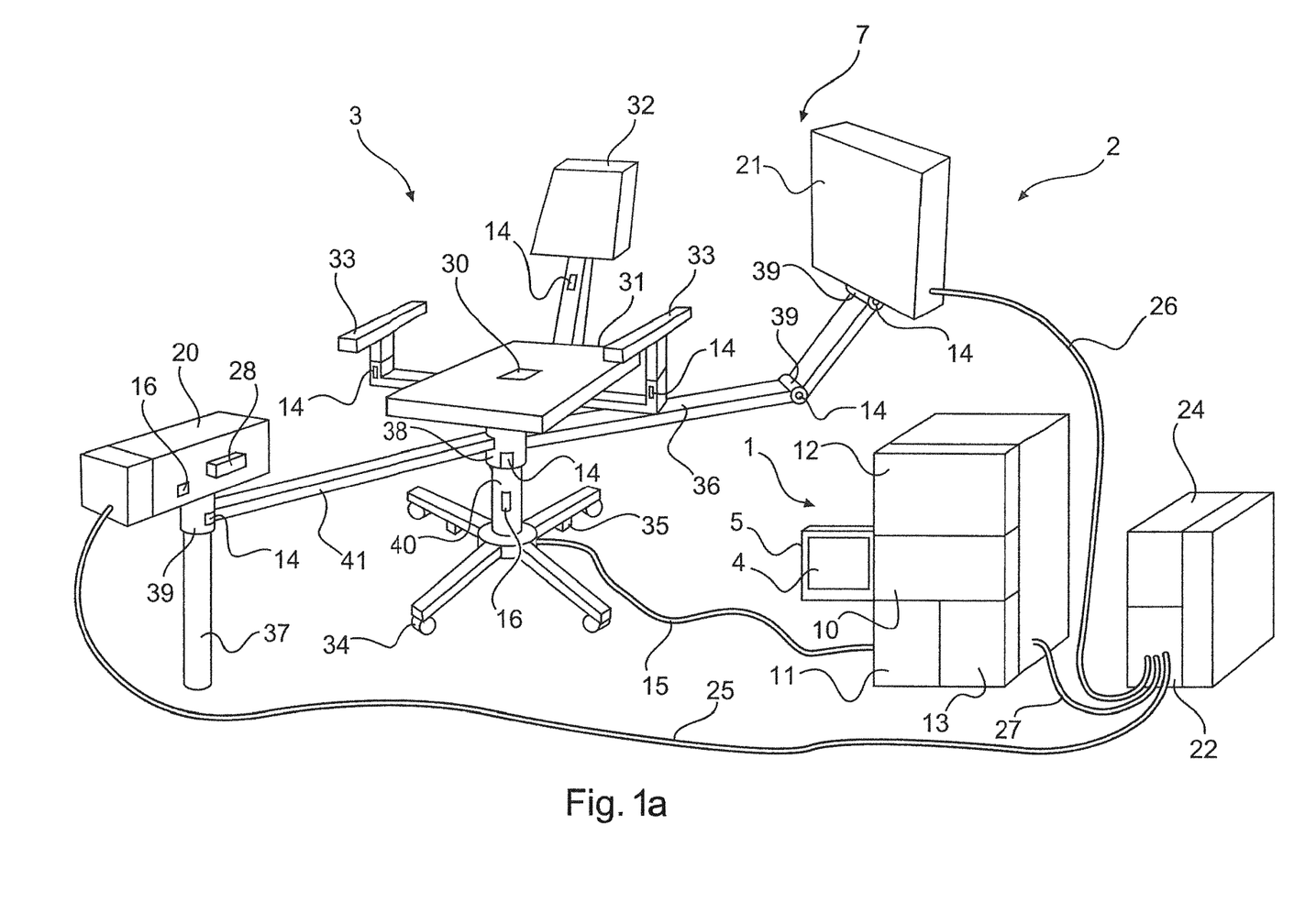
FIGS. 1a-d show schematic drawings of a device for determining positioning data for an X-ray image acquisition device on a mobile patient support unit.
Figure 1B:
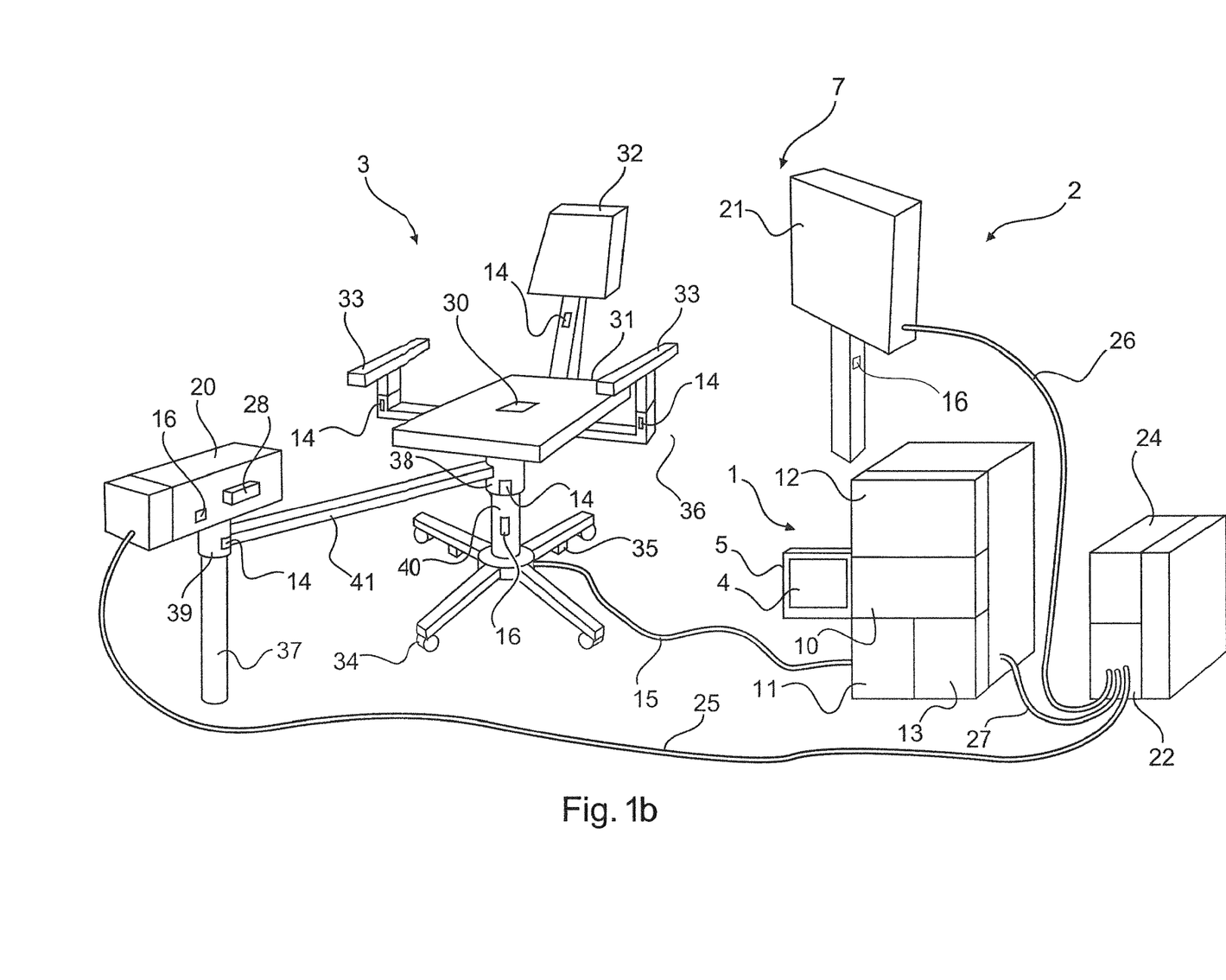
Figure 1C:
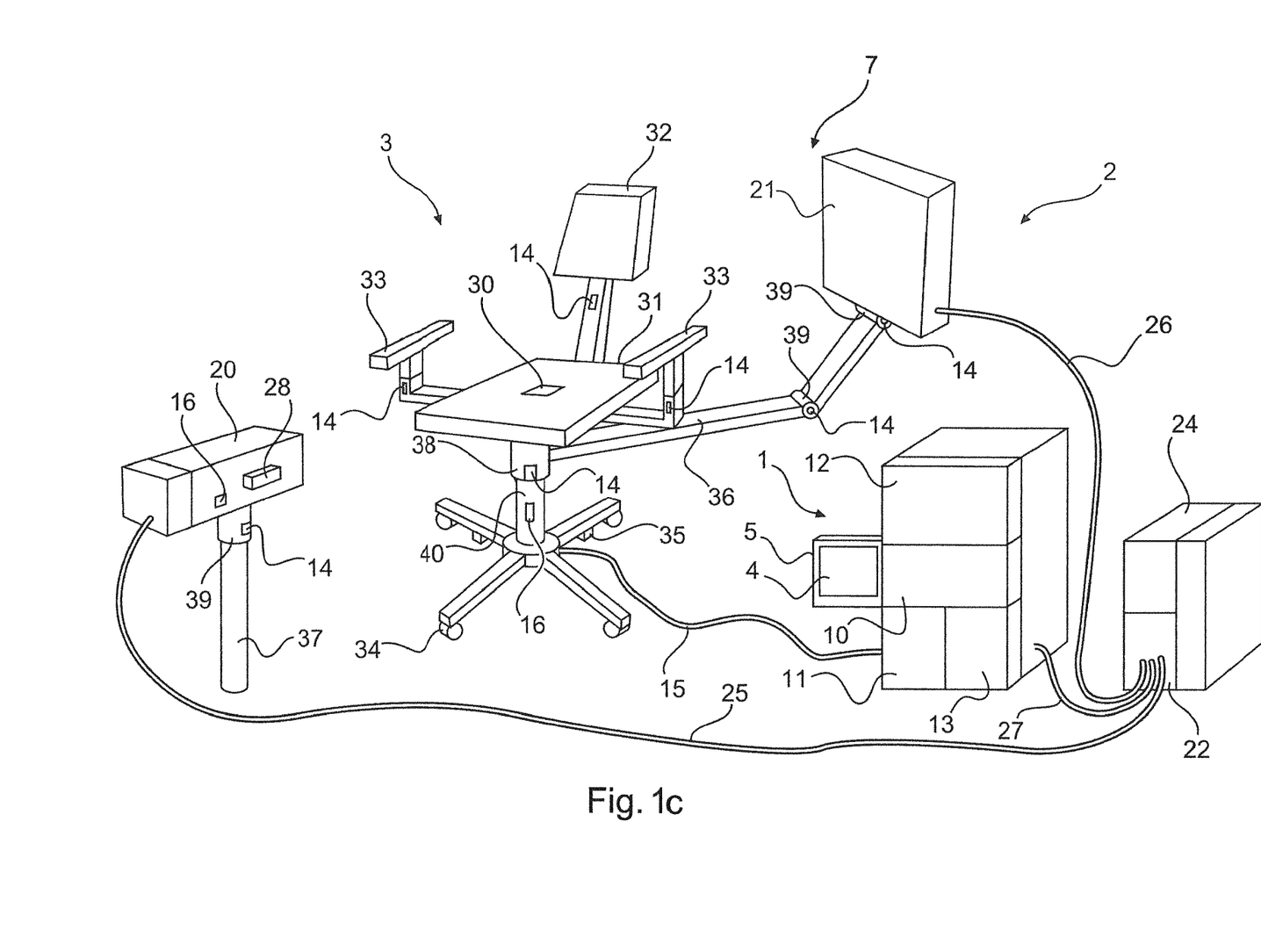

According to FIG. 1a, the components of the X-ray image acquisition device 2 may e.g. be an X-ray tube 20, an X-ray detector 21, an image data acquisition unit 22, and an image data processing unit 24. The X-Ray tube 20 and the X-Ray detector 21 may be connected to the image data acquisition unit 22 by signal cables 25, 26.

Arm 36 bears the X-ray detector 21. Arm bears X-ray tube 20. Thus, the X-ray to 20 and the X-ray detector 21 are located on different arms 36, 41. Furthermore, arms 41 and 36 may comprise a constant angular position with respect to each other, in particular an angle of 180 degree. Therefore, amending the angular position of one arm will also amend the position of the other arm.

In an alternative embodiment arm 36 and/or arm 41 may be mounted on a fixed device, e.g. a wall or a support. This means that X-ray tube 20 or X-ray detector 21 have a fixed position. If according to FIG. 1b X-ray detector 21 is fixed, then X-ray tube 20 may be adjustably mounted on the mobile patient support unit 3. If according to FIG. 1c X-ray tube 20 is fixed, then X-ray detector 21 may be adjustably mounted on the mobile patient support unit 3.

Figure 1D:
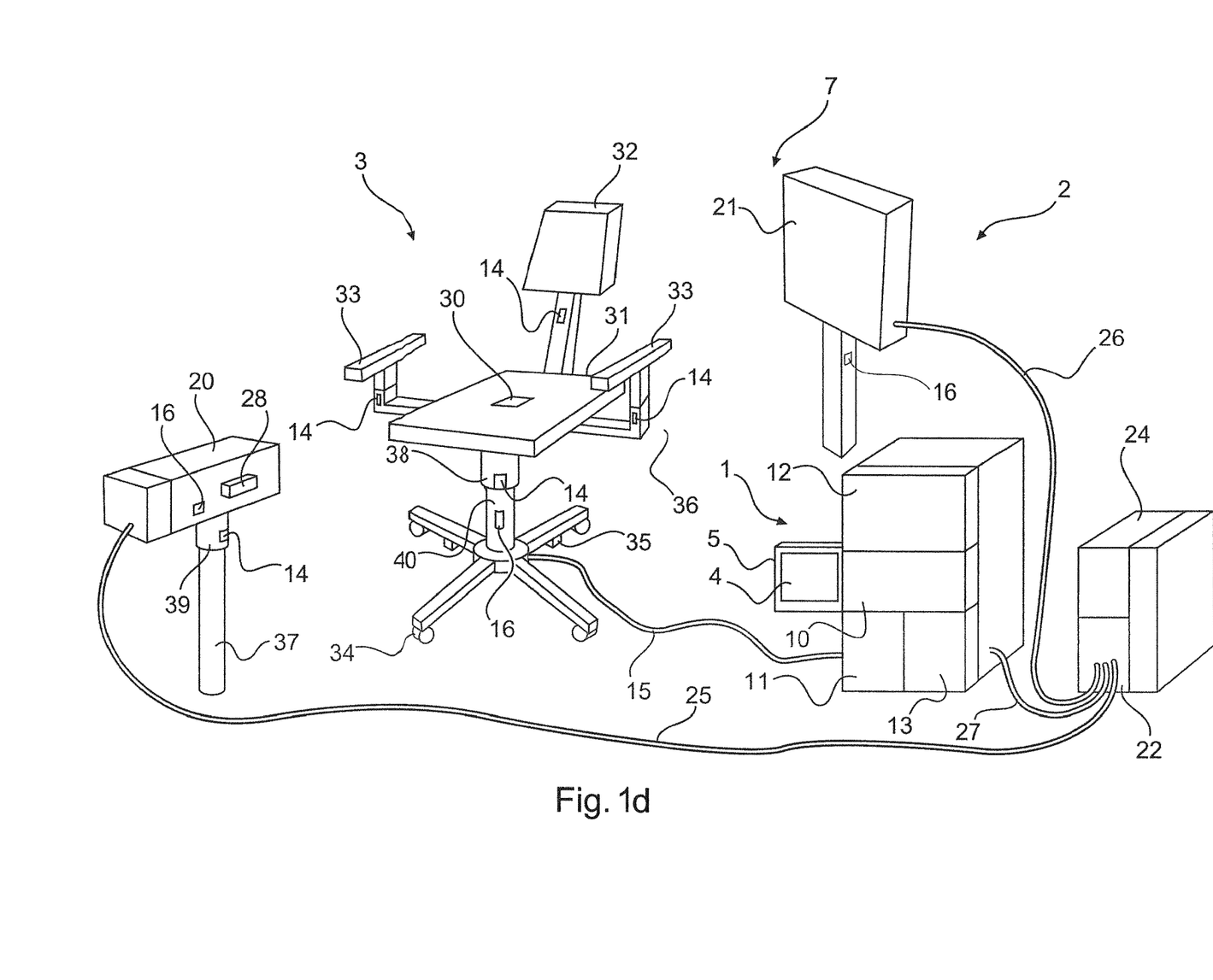

Further, according to FIG. 1d, both, X-ray tube 20 and X-ray detector 21 may be fixed. In that configuration, the distances between the X-ray tube 20 and the X-ray detector 21 is fixed. The adjustment for acquiring an X-ray image may then be performed via the positioning of the patient on the mobile support unit 3.

Furthermore, the system 7 may comprise an optical guidance unit 28. The optical guidance unit 28 may be arranged on the X-ray tube 20. In a first embodiment, the optical guidance unit 28 may provide an optical image on the X-ray detector 21. An operator may then focus the optical image on the X-ray detector 21. Focusing the optical image on the X-ray detector 21 may indicate the correct angle of the X-ray tube 20 and the correct distance between the X-ray tube 20 and the X-ray detector 21.

In an alternative or additional embodiment, the optical guidance unit 28 may comprise a laser which provides a laser-based grid. The laser-based grid may be projected on the X-ray detector 21.

The use of the laser based grid may result in a change of the size of the light grid such that the distance of the X-ray detector 21 to the X-ray tube 20 is given when the frame is fully enclosed on the X-ray detector 21 surface or corresponding to some guide or ruler. This is a very intuitive guidance. If the light frame is not fully depicted on the X-ray detector 21, the operator only requires extending the distance until it does. The use of laser grids is particularly adequate as it also allows to correct for angle errors, i.e. the distortion of the square frame.

In further alternative embodiments (not shown) further guidance tools, e.g. electronic RF based guidance, may be used.

The device 1 comprises a processing unit 10 and a status detector 11. The status detector 11 may be connected to type sensors 16 and status sensors 14. The type sensors 16 and the status sensors 14 may be arranged on the components of the X-ray image acquisition device 2 and the components of the mobile patient support unit 3.

The type sensors 16 may provide the information about the type of the component of the X-ray image acquisition device 2 or the mobile patient support unit 3, respectively. The status sensors 14 may provide the information about the status, i.e. the position, the alignment and/or the mode, of the respective component. This means if a component e.g. of the mobile patient support unit 3 is extendable then the status sensors 14 may provide the information about the extension status of that component. If the component of the mobile patient support unit 3 is a joint than the status sensor 14 may provide the information about the orientation of the joint and its components.

The status detector 11 may provide the geometry data and to type data to further components of the device 1.

The device 1 may further comprise an interface 12. An operator may provide region of interest position data to the device 1 via the interface 12. The region of interest position data indicates the position of the region of interest which shall be imaged by the X-ray image acquisition device 2.

The processing unit 10 may receive the geometry data, the type data and the region of interest position data. The processing unit 10 uses those data to determine position and alignment data as well as an image acquisition protocol for the X-ray image acquisition device 2 on the mobile patient support unit 3. Therefore, the processing unit 10 considers the geometry data, the type data and the region of interest position data to provide the operator with the information how to position and align the components of the X-ray image acquisition device 2 and the components of the mobile patient support unit 3.

Figure 2:
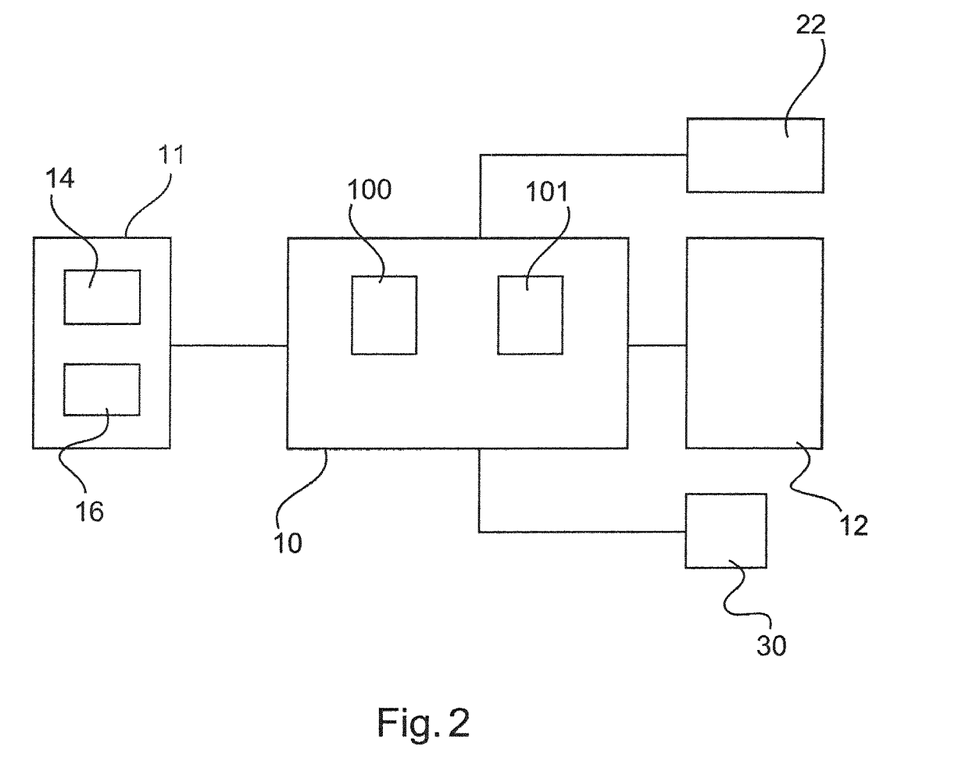
FIG. 2 shows a schematic drawing of a processing unit being connected to a movement sensor, an interface, a status detector and an image data acquisition unit.

Regarding FIG. 2, the processing unit 10 may further comprise a comparator 100. In the comparator 100 may compare the geometry data to the positioning and alignment data. That comparison by the comparator 100 may be performed continuously such that before the operator aligns and positions the components of the X-ray image acquisition device 2, the comparator 100 provides a signal which indicates that the positioning and the alignment of the components of the X-ray image acquisition device 2 is not ready for acquiring images of the region of interest. This further helps the operator to check whether the positioning and alignment of the components of the X-ray image acquisition device 2 is correct or whether the operator should further position and align those components.

Furthermore, the processing unit 10 may comprise an optimization module 101 which is configured to optimize the positioning and alignment data and provide an optimal image acquisition protocol. The optimization module 101 is uses the geometry data, the type data and the region of interest position data to optimize the position and alignment data and the determination of the optimal image acquisition protocol. The optimization module 101 may perform a simulation of the image acquisition and based on that simulation the optimization module 101 may alter the variables, e.g. the time duration of the provisioning of X-ray radiation, the intensity of the X-ray radiation, the distances between the components of the X-ray image acquisition device 2 and the region of interest, the distances between the components of the X-ray image acquisition device 2 and the mobile patient support unit 3, and/or the angles of the components of the X-ray image acquisition device 2 and the components of the mobile patient support unit 3, until the simulated image has the optimized properties for showing the region of interest.

The processing unit 10 may further be connected to the interface 12 and the status detector 11. Furthermore, the processing unit may be connected to the image data acquisition unit 22 of the X-ray image acquisition device 2 and/or to the movement sensor 30 which may be attached to the mobile patient support unit 3.

The processing unit 10 may be configured to perform the method 6. Therefore, the processing unit 10 may be configured to perform the following steps.

In a step 60, geometry data and type data of the mobile patient support unit 3 is acquired with a status detector 11. The geometry data comprises the position of the components of the X-ray image acquisition device 2 and the mobile patient support unit 3 in relation to the mobile patient support unit 3. The status detector 11 may collect the geometry data and the type data by questioning geometry sensors 14 and type sensors 16 which are located at the X-ray image acquisition device 2 and the mobile patient support unit 3.

In a further step 61 data about a region of interest position on the patient is acquired. That region of interest may be e.g. a patient's arm, leg or further organ which may be indicated by an operator. The position of that region of interest is then related to the mobile patient support unit 3. With steps 60 and 61 the relevant positions which are needed for the adjustment of the components of the X-ray image acquisition device 2 and the mobile patient support unit 3 may be acquired.

Steps 60 and 61 may be performed at the same time or in any order. It does not matter if the acquisition of the region of interest position data is performed before the acquisition of the geometry data and the type data of the mobile patient support unit 3 and the X-ray image acquisition device 2.

Furthermore, in a further step 62 positioning and alignment data for the X-ray image acquisition device 2 on the mobile patient support unit 3 are determined considering region of interest position data of step 61, the geometry data and the type data being acquired in step 60. Therefore, the method 6 provides the information about the positioning and the alignment for the X-ray image acquisition device components. Using that information, the operator may position and align the X-ray image acquisition device 2 according to the positioning and alignment data to ensure that the acquired image shows the region of interest in the correct magnification and in adequate quality.

In a further step 63 the method provides an image acquisition protocol for the X-ray image acquisition device 2 based on the region of interest position data, the geometry data and the type data. The image acquisition protocol for the X-ray image acquisition device 2 provides the parameters for the image acquisition with the X-ray image acquisition device 2. The image acquisition protocol may for example comprise the values for the voltage and the current for the spectrum and the flux together with the operation time of the X-ray radiation source to determine the X-ray radiation intensity needed for the image acquisition or the time duration for applying the X-ray radiation on the region of interest position.

The provisioning of the image acquisition protocol step 63 may comprise sub-steps. Thereby, in a sub-step 64, an optimized positioning and alignment data and the optimal image acquisition protocol based on the status signal may be determined. This means, that the method performs a check on the image acquisition protocol and the positioning and alignment data. Further, the method may simulate the result of the image acquisition. Based on the simulation the image acquisition protocol and the positioning and alignment data may be altered until the simulation provides the result that an optimized image will be acquired.

In a further sub-step 65, the corresponding image acquisition protocol and positioning and alignment data is then determined to be the optimized positioning and alignment data and the optimal image acquisition protocol.

In a further step 66 after step 63, the positioning and alignment data may be provided to an operator by an interface. The operator may then position and align the X-ray image acquisition device 2 based on the position and alignment data which the interface communicates to the operator.

Alternatively, the positioning and alignment data may be used to automatically position and align the components of the X-ray image acquisition device 2. This may further simplify the image acquisition with an X-ray image acquisition device 2.

The method may further comprise the step 67 wherein the geometry data is compared to the positioning and alignment data with a comparator. This comparison may provide any deviations between the positioning and alignment data and the geometry data, wherein the geometry data provides the actual position and alignment of the components of the X-ray image acquisition device 2 and the mobile patient support unit 3. If the deviations are within a threshold interval, the comparison may result that the geometry data match the positioning and alignment data. If not, the comparison would result that the geometry data does not match the positioning and alignment data.

The result may be communicated in a further step 68 in which a result signal comprising the information whether the jump to data matches the positioning and alignment data is provided. If the geometry data does not match the positioning and alignment data, the signal may be an alarm signal which may alarm the operator that the components of the X-ray image acquisition device are not correctly positioned and aligned. Furthermore, the signal according to step 68 may provide a confirmation signal providing the information that the components of the X-ray image acquisition device 2 are correctly aligned and positioned according to the positioning and alignment data.

Furthermore, the method may comprise a step 70 in which a patient's movement on the mobile patient support unit 3 is determined. The determination of the movement of the patient may be performed by a movement sensor 30. The information about the patient's movement may be used in a step 71 in which the point of time for acquiring an X-ray image of the patient is determined. The determination of the point of time for acquiring an X-ray image of the patient may consider how much the patient moves. If the patient moves much then the point of time for acquiring the X-ray image is delayed. The point of time for the acquisition of the X-ray image may be set to the actual point of time, if the patient does not move much. Therefore, that determination of the point of time for the image acquisition may avoid blurring or a reduced image quality due to movements by the patient.

In another exemplary embodiment of the present invention, a computer program 4 or a computer program element is provided, that is characterized by being adapted to execute the method steps of the method 6 according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program 4 that right from the beginning uses the invention and a computer program 4 that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium 5, such as a CD-ROM, is presented wherein the computer readable medium 5 has a computer program element 4 stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for determining positioning for an X-ray image acquisition device on a mobile patient support, the device comprising:
   a processor; and
   a status detector;
   wherein the status detector is configured to acquire geometry data and type data of a mobile patient support and of an X-ray image acquisition device, wherein the geometry data comprises spatial position, angular orientation and alignment data of components of the X-ray image acquisition device in relation to the mobile patient support that comprises at least two support devices, and the at least two support devices comprise a joint connector and/or a rotational bearing element, wherein the rotational bearing element is connected to the mobile patient support, wherein at least one of the at least two support devices is movably attached to the mobile patient support, wherein the components of the X-ray image acquisition device comprise, an X-ray tube and an X-ray detector, and wherein at least one of the at least two support devices is attached to the X-ray tube, and the at least one of the remaining support devices is attached to the X-ray detector;
   wherein the status detector is configured to transmit a status signal comprising the geometry data and the type data;
   wherein the processor is configured to receive the status signal and a region of interest position on a patient; and
   wherein, based on the status signal and the region of interest position, the processor is configured to determine the spatial position, angular orientation and alignment data for the components of the X-ray image acquisition device in relation to the mobile patient support, and to provide an image acquisition protocol for the X-ray image acquisition device.

2. The device according to claim 1, wherein the device further comprises
   an interface
   configured to provide the spatial position, angular orientation and alignment data to an operator and/or receive data about the region of interest position on the patient.

3. The device according to claim 1, wherein the processor further comprises:
   a comparator
   configured to compare the geometry data and the spatial position, angular orientation and alignment data and provide a result signal indicating whether the geometry data matches the spatial position, angular orientation and alignment data.

4. The device according to claim 1, wherein the processor comprises:
   an optimization module
   configured to determine an optimized spatial position, angular orientation and alignment data and an optimal image acquisition protocol based on the status signal and the region of interest position; and
   wherein the processor is configured to provide an image acquisition protocol based on the optimal image acquisition protocol.

5. A system for determining positioning data for an X-ray image acquisition device on a mobile patient support, the system comprising:
   a mobile patient support;
   an X-ray image acquisition system; and
   a device comprising:
      a processor; and
      a status detector;
      wherein the status detector is configured to acquire geometry data and type data of a mobile patient support and of an X-ray image acquisition device, wherein the geometry data comprises spatial position, angular orientation and alignment data of components of the X-ray image acquisition device in relation to the mobile patient support that comprises at least two support devices, and the at least two support devices comprise a joint connector and/or a rotational bearing element, wherein the rotational bearing element is connected to the mobile patient support, wherein the components of the X-ray image acquisition device comprise an X-ray tube and an X-ray detector, and wherein at least one of the at least two support devices is attached to the X-ray tube, and the at least one of the remaining support devices is attached to the X-ray detector;

wherein the status detector is configured to transmit a status signal comprising the geometry data and the type data;

wherein the processor is configured to receive the status signal and a region of interest position on a patient; and wherein, based on the status signal and the region of interest position, the processor is configured to determine the spatial position, angular orientation and alignment data for the components of the X-ray image acquisition device in relation to the mobile patient support, and to provide an image acquisition protocol for the X-ray image acquisition device.

6. The system according to claim 5, wherein the mobile patient support comprises:

a movement sensor configured to determine a patient's movement on the mobile patient support and provide a movement signal; and wherein the processor is configured to receive the movement signal and determine a point of time for acquiring an X-ray image based on the movement signal.

7. The system according to claim 6, wherein at least one of the at least two support devices is movably attached to the mobile patient support or each of the at least two support devices configured to provide a fixed mounting for the X-ray tube and the X-ray detector.

8. A method for determining positioning for an X-ray image acquisition device on a mobile patient support, the method comprising:

acquiring geometry data and type data of a mobile patient support unit and of an X-ray image acquisition device using a status detector, wherein the geometry data comprises spatial position, angular orientation and alignment data of components of the X-ray image acquisition device in relation to the mobile support that comprises at least two support devices, and the at least two support devices comprise a joint connector and/or a rotational bearing element, wherein the rotational bearing element is connected to the mobile patient support, wherein at least one of the at least two support devices is movably attached to the mobile patient support, wherein the components of the X-ray image acquisition device comprise an X-ray tube and an X-ray detector, and wherein at least one of the at least two support devices is attached to the X-ray tube and the at least one of the remaining support devices is attached to the X-ray detector;

acquiring a region of interest position on a patient;

determining the spatial position, angular orientation and alignment data for the X-ray image acquisition device on the mobile patient support based on the region of interest position, the geometry data and the type data; and providing an image acquisition protocol for the X-ray image acquisition device based on the region of interest position, the geometry data and the type data.

9. The method according to claim 8, further comprising:

providing the spatial position, angular orientation and alignment data to an operator via an interface.

10. The methodMethod according to claim 8, further comprising:

comparing the geometry data and the spatial position, angular orientation and alignment data using a comparator; and providing a result signal indicating whether the geometry data matches the spatial position, angular orientation and alignment data.

11. The method according to claim 8, further comprising:

determining an optimized spatial position, angular orientation and alignment data and an optimal image acquisition protocol based on the status signal; and determining an image acquisition protocol based on the optimal image acquisition protocol.

12. The method according to claim 8, further comprising:

determining a patient's movement on the mobile patient support; and determining a point of time for acquiring an X-ray image of the patient.

13. A non-transitory computer-readable medium having one or more executable instructions stored thereon which, when executed by at least one processor, cause the at least one processor to perform a method for determining positioning for an X-ray image acquisition device on a mobile patient support, the method comprising:

acquiring geometry data and type data of a mobile patient support unit and of an X-ray image acquisition device using a status detector, wherein the geometry data comprises spatial position, angular orientation and alignment data of components of the X-ray image acquisition device in relation to the mobile support that comprises at least two support devices, and the at least two support devices comprise a joint connector and/or a rotational bearing element, wherein the rotational bearing element is connected to the mobile patient support, wherein at least one of the at least two support devices is movably attached to the mobile patient support, wherein the components of the X-ray image acquisition device comprise an X-ray tube and an X-ray detector, and wherein at least one of the at least two support devices is attached to the X-ray tube and the at least one of the remaining support devices is attached to the X-ray detector;

acquiring a region of interest position on a patient;

determining the spatial position, angular orientation and alignment data for the X-ray image acquisition device on the mobile patient support based on the region of interest position, the geometry data and the type data; and providing an image acquisition protocol for the X-ray image acquisition device based on the region of interest position, the geometry data and the type data.

* * * * *